US005562694A

United States Patent [19]

Sauer et al.

[11] Patent Number: 5,562,694
[45] Date of Patent: Oct. 8, 1996

[54] MORCELLATOR

[75] Inventors: Jude S. Sauer, Pittsford; Roger J. Greenwald, Holley; Mark A. Bovard, Williamson; John F. Hammond, Canandaigua, all of N.Y.

[73] Assignee: LaserSurge, Inc., Rochester, N.Y.

[21] Appl. No.: 321,367

[22] Filed: Oct. 11, 1994

[51] Int. Cl.$^6$ .......................... A61B 17/14; A61B 17/32; A61B 17/28
[52] U.S. Cl. .......................... 606/176; 606/167; 606/205
[58] Field of Search .................................. 128/749–754; 606/1, 106, 110, 127, 167, 170, 171, 174–179, 184, 185, 205–208

[56] References Cited

U.S. PATENT DOCUMENTS

| | | | |
|---|---|---|---|
| 2,540,936 | 2/1951 | Daniels | 606/110 |
| 4,111,207 | 9/1978 | Seiler, Jr. . | |
| 4,282,884 | 8/1981 | Boebel . | |
| 4,428,375 | 1/1984 | Ellman . | |
| 4,589,414 | 5/1986 | Yoshida et al. . | |
| 4,649,919 | 3/1987 | Thimsen et al. . | |
| 4,651,753 | 3/1987 | Lifton . | |
| 4,830,000 | 5/1989 | Shutt . | |
| 4,844,064 | 7/1989 | Thimsen et al. . | |
| 4,850,354 | 7/1989 | McGurk-Burleson et al. . | |
| 4,867,157 | 9/1989 | McGurk-Burleson et al. . | |
| 4,936,313 | 6/1990 | Burkhardt et al. . | |
| 4,994,024 | 2/1991 | Falk . | |
| 5,007,917 | 4/1991 | Evans . | |
| 5,084,052 | 1/1992 | Jacobs . | |
| 5,106,364 | 4/1992 | Hayafuji et al. . | |
| 5,176,687 | 1/1993 | Hasson et al. | 606/127 |
| 5,176,695 | 1/1993 | Dulebohn | 606/170 |
| 5,190,561 | 3/1993 | Graber | 606/127 |
| 5,195,954 | 3/1993 | Schnepp-Pesch et al. . | |
| 5,207,697 | 5/1993 | Carusillo et al. . | |
| 5,215,521 | 6/1993 | Cochran et al. . | |
| 5,217,479 | 6/1993 | Shuler . | |
| 5,224,930 | 7/1993 | Spaeth et al. . | |
| 5,226,910 | 7/1993 | Kajiyama et al. . | |
| 5,234,453 | 8/1993 | Smith et al. . | |
| 5,242,460 | 9/1993 | Klein et al. . | |
| 5,269,785 | 12/1993 | Bonutti . | |
| 5,275,609 | 1/1994 | Pingleton et al. . | |
| 5,281,230 | 1/1994 | Meidmueller | 606/208 |
| 5,290,303 | 3/1994 | Pingleton et al. . | |
| 5,300,087 | 4/1994 | Knoepfler | 606/205 |
| 5,301,684 | 4/1994 | Ogirala . | |
| 5,304,124 | 4/1994 | Essig et al. . | |
| 5,304,181 | 4/1994 | Caspari et al. . | |
| 5,318,589 | 6/1994 | Lichtman | 606/205 |
| 5,320,627 | 6/1994 | Sorensen et al. | 606/127 |
| 5,324,301 | 6/1994 | Drucker . | |
| 5,335,671 | 8/1994 | Clement . | |
| 5,439,474 | 8/1995 | Li | 606/184 |

FOREIGN PATENT DOCUMENTS

| | | | |
|---|---|---|---|
| 0621008 | 10/1994 | European Pat. Off. . | |
| 9415533 | 7/1994 | WIPO | 606/206 |

OTHER PUBLICATIONS

Cushieri, A. et al., *Slicer and Tissue Retrieval System for Excisional Endoscopic Surgery*, Surgical Endoscopy vol. 8, 1246–1249 (1994).
*Slicer and Tissue Retrieval System for Excisional Endoscopic Surgery*, Surgical Endoscopy, 1994, pp. 1246–1249.

Primary Examiner—Gary Jackson
Assistant Examiner—Glenn Dawson
Attorney, Agent, or Firm—Cumpston & Shaw

[57] ABSTRACT

A surgical instrument is provided for the morcellation of bodily tissue or bodily organ parts during an endoscopic surgical procedure. The instrument includes a handle assembly and a tubular body portion extending from the handle assembly and defining a longitudinal axis. A tool assembly is associated with a distal end of the tubular body including cooperating jaw members and a cutting member. A first mechanism is for effectuating remote actuation of the cooperating jaw members and a second mechanism is for effectuating remote reciprocal movement of the cutting member with respect to the longitudinal axis of the tubular body.

23 Claims, 7 Drawing Sheets

MORCELLATOR

BACKGROUND

1. Technical Field

The subject application relates to a surgical apparatus for fragmenting and removing tissue or bodily organ parts during surgery, and is particularly adapted to use during endoscopic surgical procedures.

2. Background of Related Art

One of the recent advances in the surgical area has been endoscopic surgery which in many cases reduces the invasiveness of a surgical procedure and overall patient trauma. Generally, endoscopic surgery involves incising through body walls for examining, viewing and/or operating on various bodily organs or structures, including the ovaries, uterus, gall bladder, bowels, kidneys, appendix, etc. In endoscopic procedures, a trocar typically creates an incision and trocar tubes or cannula devices are extended into and left in place in the abdominal wall so that endoscopic surgical tools may be inserted through the trocar cannula. A camera or endoscope is inserted through the trocar cannula which, is generally located at the navel incision, thereby enabling the visual inspection and magnification of a cavity in the body. The surgeon then performs the desired procedure at the surgical site with the aid of specialized instrumentation designed to fit through additional trocar cannulas which provide additional entries into the desired body cavity. Thus, instead of a rather large incision (typically 12 inches or larger) necessary to complete a fully invasive surgical procedure, endoscopic surgery results in several smaller incisions, usually between 5 and 15 millimeters in size. In most instances, recovery is quicker and less painful than traditional surgery. In addition, because the surgical field is greatly magnified surgeons are often better able to dissect blood vessels and control blood loss. In addition, heat and water loss are often reduced as a result of the smaller incisions.

In many surgical procedures, it is often necessary to remove tissue or diseased organs. This is especially challenging during endoscopic surgery because the tissue or organ removal must be achieved through the small openings through which the procedure is performed. In these situations it may be desirable to fragment, or morcellate, or cut into smaller segments the bodily tissue so that it can be readily removed through the small endoscopic openings.

Morcellation involves fragmenting and removing diseased tissue or organ parts from healthy tissue or organs. In endoscopic morcellation, the fragmented pieces are typically removed from the patient's body through a small incision or through a trocar cannula device which extends through the abdominal wall. When the tissue or organ part is diseased or infected, it is preferred that the excised portions thereof be isolated from contact with surrounding healthy tissue. Accordingly, it is often necessary to enclose the fragmented organ during removal, thus preventing contamination of healthy tissue and bodily organs. A device for accomplishing such a task is disclosed in U.S. Pat. No. 4,428,375 which describes a drawstring bag for encapsulating a fragmented organ during surgical repair. In some instances, the organ is fragmented in the bag by a surgical device known as a morcellator, until such a time as the entire specimen is small enough to be removed while in the bag, from the abdominal cavity, via the trocar cannula.

Once the diseased tissue or organ has been fragmented and removed from the body cavity, it is often necessary to reconstruct the fragmented tissue pieces into their original orientation for pathologic evaluation. A subsequent examination of the reconstructed tissue enables, and is often necessary for, a precise diagnosis of the patient's ailment. However, to facilitate the reconstruction of the tissue part, the fragmented tissue pieces must be of a suitable size and shape.

Generally, there are two types of endoscopic morcellators, manually operated and electrically assisted. Manually operated morcellators are typically operated by a hand lever connected to an elongated endoscopic member. The distal end of the endoscopic member is connected to cutting members which are operatively associated through the endoscopic member with the hand lever. In use, the manually operated morcellator is advanced to the surgical site where the tissue or bodily organ part to be separated is positioned between the cutting members. The surgeon then actuates the cutting members to cut the tissue or organ part. If the removal of the tissue or organ is being performed without a surgical bag, the surgeon must repeatedly remove the morcellator completely from the abdominal cavity to remove the fragmented tissue or bodily organ part from the cutting member and then reinsert the morcellator, via the trocar cannula, back to the surgical site to remove a further tissue or organ part. If the removed tissue or organ is diseased or infected, it may be necessary to place the organ in a surgical bag prior to fragmentation and removal. When the surgical bag is employed, the cutting edges of the morcellator cannot cut the surgical bag because such would result in tearing the bag and potentially exposing diseased tissue to healthy body tissue.

Electric morcellators are generally used in conjunction with a surgical bag and are typically provided with a high speed cutting blade that rapidly fragments the tissue or organ into very small pieces within the bag to enhance removability. The fragmented tissue or organ can then be aspirated from the bag, or the entire bag may be removed containing the fragmented tissue. One such electric morcellator is described in U.S. Pat. No. 5,215,521 to Cochran et at.

Such electric morcellators may disadvantageously result in the rotating cutting blade cutting the surgical bag, thus risking the possibility that healthy tissue surrounding the surgical bag may become contaminated by the resulting leakage. Additionally, the tissue or organ parts which are fragmented by the electric morcellator may be insufficiently sized to undergo a proper pathologic evaluation.

Thus, there exists a need for an endoscopic morcellator which is easy to operate, capable of aiding in the removal of diseased tissue without infecting surrounding healthy tissue, and which fragments tissue in manner which allows the pieces to be of a sufficient size to undergo a proper pathologic evaluation.

SUMMARY

Because endoscopic procedures are more common than laparoscopic procedures, the present application utilizes terms of endoscopic procedures and apparatus. However, use herein of terms such as "endoscopic", "endoscopically", and "endoscopic portion", among others, should not be construed as limited to an apparatus for use only in conjunction with an endoscopic tube. To the contrary, it is believed that the apparatus described herein may find use in other procedures wherein access is limited to a small incision, such as, for example laparoscopic or arthroscopic procedures.

The present application is directed to a surgical apparatus having a pair of cooperating jaw members and a cutting member for cutting and removing tissue or organ parts during an endoscopic procedure. The apparatus includes a handle assembly, an elongated body portion extending from the handle assembly and defining a longitudinal axis, and a tool assembly associated with a distal end portion of the elongated body portion. The tool assembly includes the pair of cooperating jaw members and the cutting member. More particularly, the cutting member is positioned within an internal cavity being defined by the cooperating jaw members. The surgical apparatus further includes a first actuation mechanism for remotely actuating the cooperating jaw members between a closed position substantially parallel to the longitudinal axis of the elongated body portion and an open position, such that at least one jaw member is disposed angularly with respect to the longitudinal axis of the elongated body portion in the open position. A second actuation mechanism is also provided for actuating the cutting member relative to the cooperating jaw members.

In a preferred embodiment, the second actuation mechanism for actuating the cutting member includes a handle member and actuation arms which interconnect the cutting member to the handle member which is operatively associated with the handle assembly. The reciprocal movement of the cutting member is preferably achieved through movement of the handle member which causes the actuation arms to translate reciprocatingly with respect to a transverse axis of the body portion.

The first actuation mechanism for effectuating the remote actuation of the cooperating jaw members preferably includes a trigger member and at least one linkage member which interconnects at least one of the cooperating jaw members to the trigger member which is operatively associated with the handle assembly. Jaw actuation is achieved by causing reciprocating longitudinal movement of the linkage members through manipulation of the trigger portion.

Preferably, the elongated body portion of the surgical apparatus is provided with a bore extending therethrough which is configured to enable a surgical instrument to pass through the bore defined in the elongated portion. The bore should also have a suitable diameter so as to allow the passage of tissue samples therethrough. The surgical instrument is configured to extend through the bore of the elongated body portion and preferably includes an elongated member having opposing distal and proximal ends. The distal end of the elongated member of the surgical instrument includes a tool assembly preferably configured and adapted to engage and/or grasp tissue. The proximal end preferably includes a handle mechanism to effectuate actuation of the tool assembly to engage and/or grasp the tissue. Thus, tissue samples can be removed through the bore of the instrument without removing the entire instrument from its position within the patient.

The surgical apparatus described herein is particularly adapted for use during endoscopic surgical techniques. However, it is to be appreciated that the surgical apparatus can be used during any operative procedure requiring the fragmentation and removal of tissue or organ parts. Further features of the surgical apparatus described herein will become more readily apparent from the following detailed description taken in conjunction with the accompanying drawings.

BRIEF DESCRIPTION OF THE DRAWINGS

Various embodiments are described herein with reference to the drawings wherein.

DETAILED DESCRIPTION OF THE PREFERRED EMBODIMENT(S)

In the drawings and in the description which follows, the term "proximal", as is traditional, will refer to the end of the surgical apparatus which is closest to the operator, while the term "distal" will refer to the end of the apparatus which is furthest from the operator.

Figure 1:
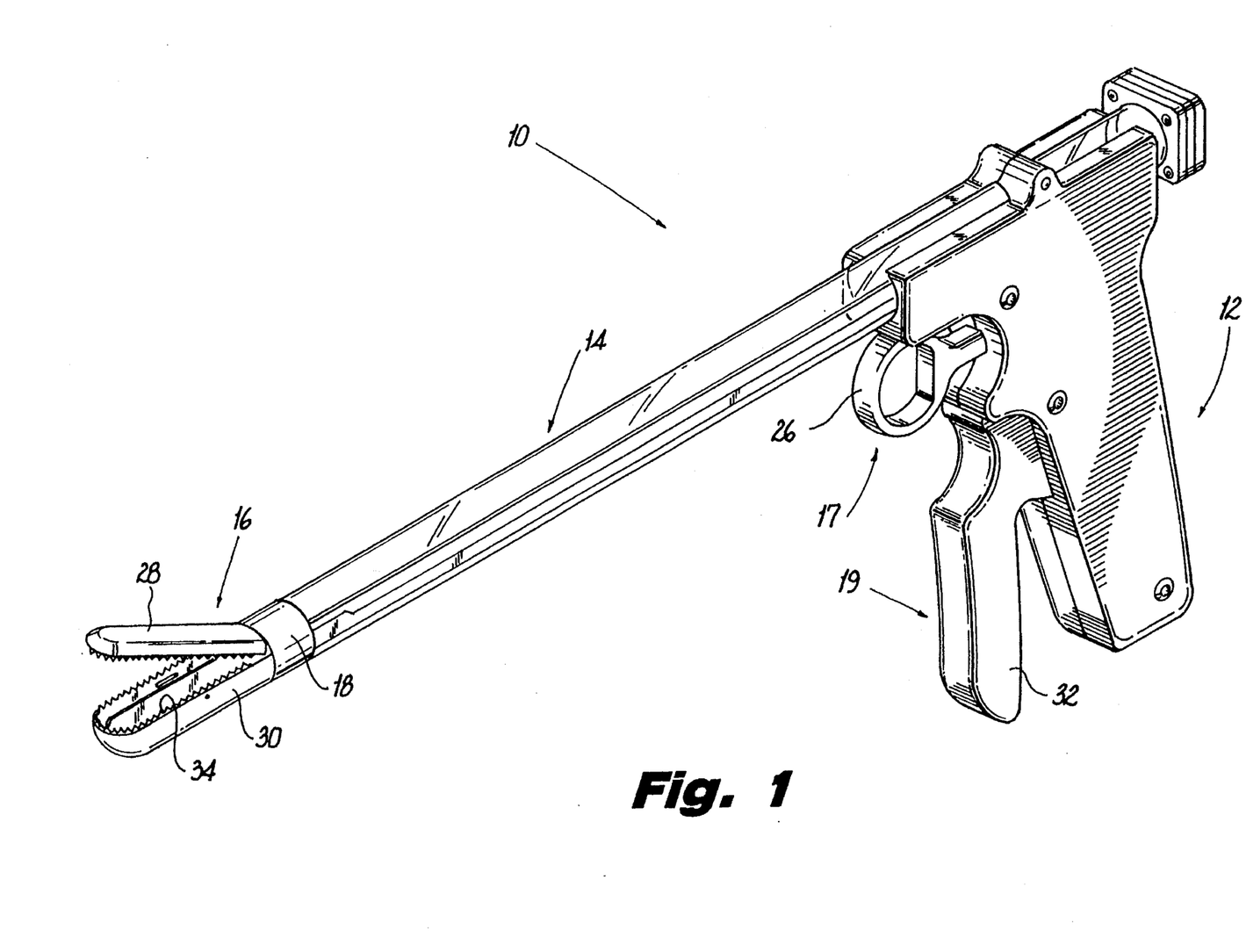
FIG. 1 is a perspective view of a surgical morcellator apparatus.

An embodiment of the surgical apparatus of the subject application is illustrated in FIG. 1 and is designated generally by reference numeral 10. Surgical apparatus 10 is configured for fragmenting tissue during endoscopic procedures in which access to the surgical site is limited. In brief, the surgical instrument 10 includes a handle assembly 12, an elongated body portion 14 extending longitudinally from the handle assembly 12 and preferably dimensioned for endoscopic use, and a tool assembly 16 operatively associated with the distal end 18 of the elongated body portion 14.

The surgical apparatus 10 is particularly adapted to enable the surgeon, preferably with the employment of a surgical grasping instrument 400 (See FIG. 4), to access and draw target tissue into the tool assembly 16 of the surgical instrument 10. The user can then retain the target tissue in the tool assembly 16 through use of a first actuation mechanism generally designated by reference numeral 17 and fragment the target tissue through use of a second actuation mechanism generally designated by reference numeral 19.

The first actuation mechanism 17 includes a trigger member 26 associated with the handle assembly 12 which effectuates actuation of upper and lower cooperating jaw members 28, 30 between an open position and closed position. The second actuation mechanism 19 includes a handle member 32 associated with the handle assembly 12 for effectuating reciprocal translation of blade cutting member 34, relative to the longitudinal axis defined by the elongated body portion 14. Each of these mechanisms, which effectuates the holding and then fragmenting of tissue at a target site, will be discussed in greater detail hereinbelow.

Figure 2:
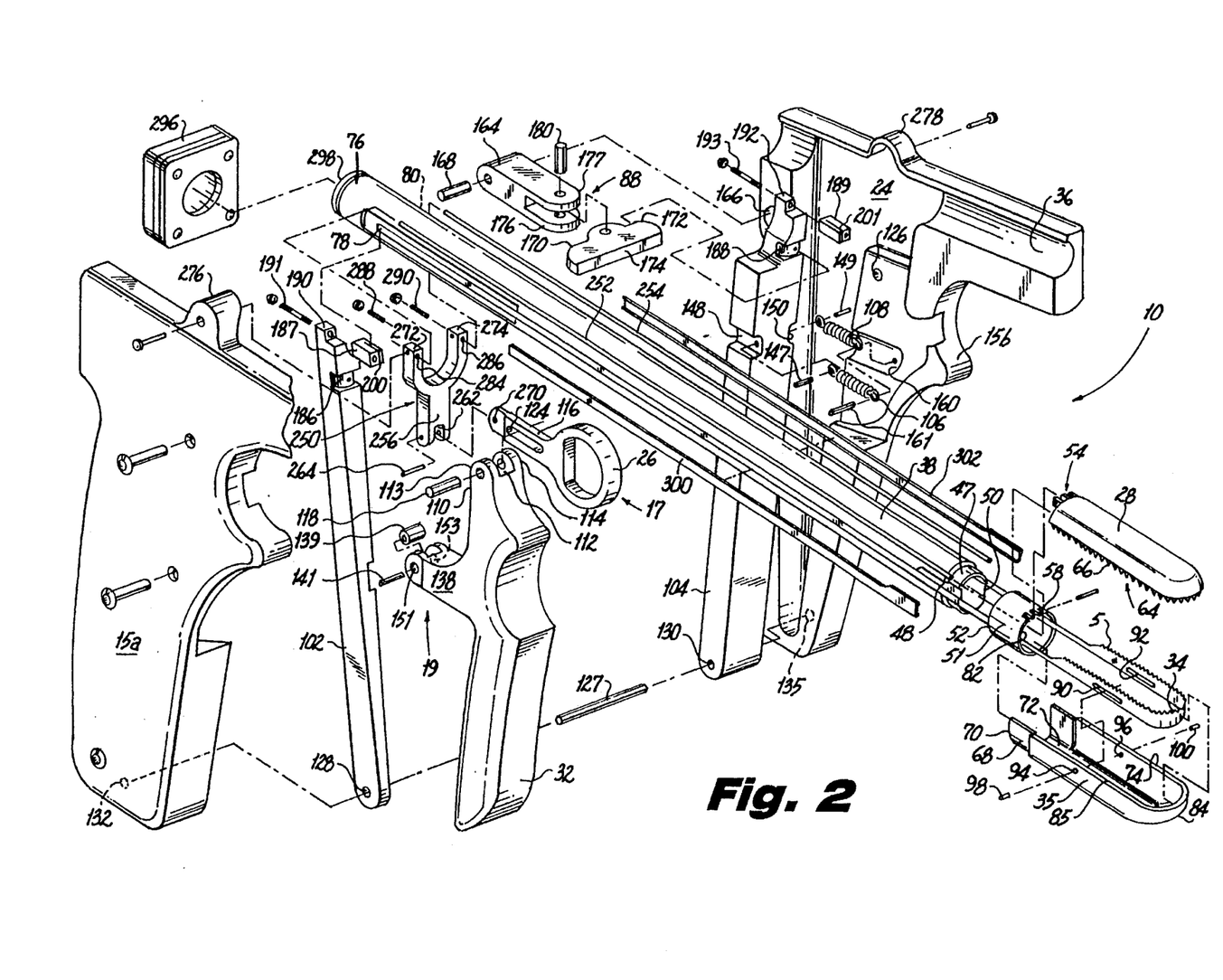
FIG. 2 is an exploded perspective view of the surgical morcellator apparatus of FIG. 1.
Figure 3:
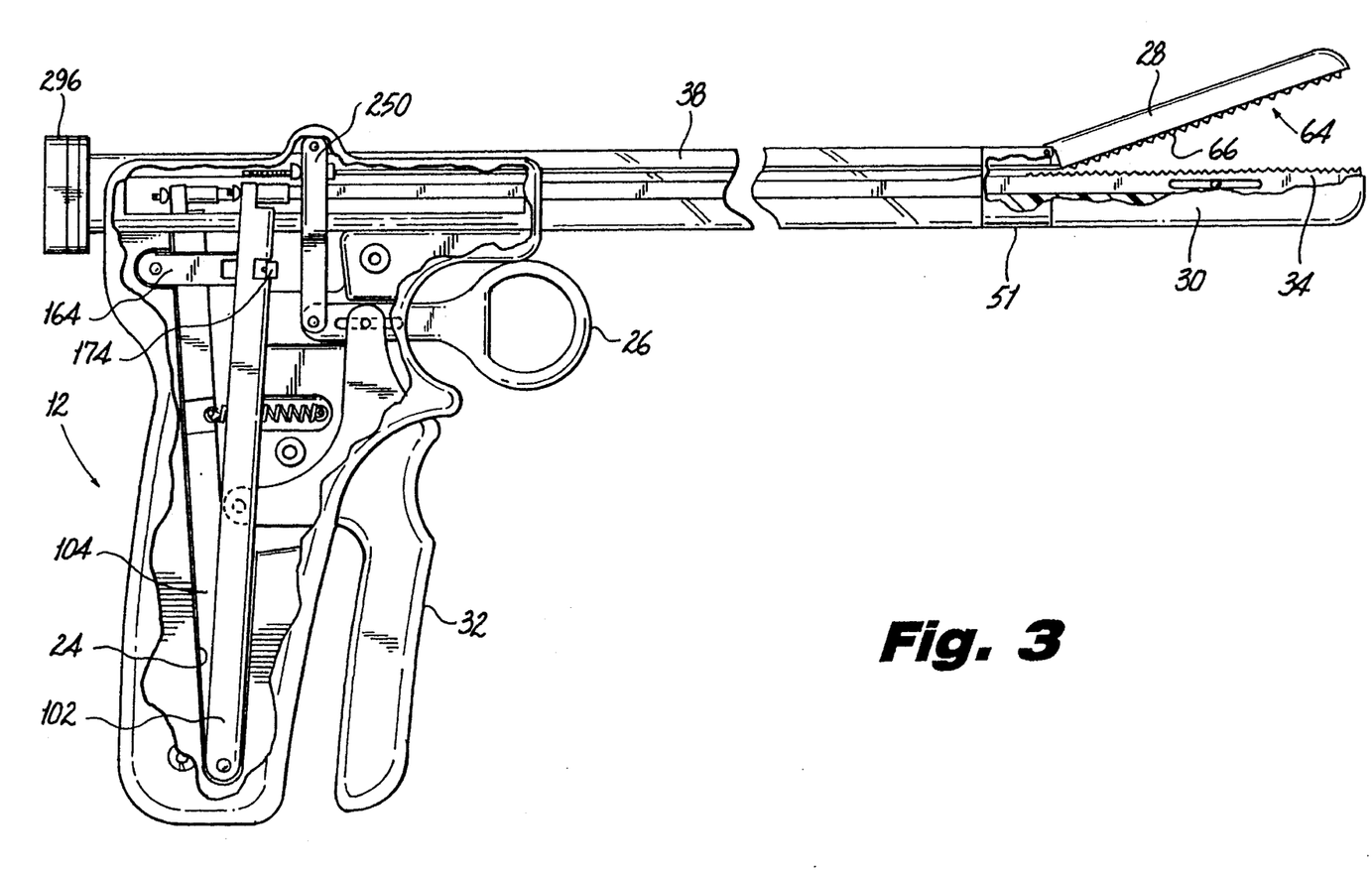
FIG. 3 is a side elevational view in partial cross-section of the surgical morcellator apparatus of FIG. 1 with the upper jaw in an open position.

Referring to FIGS. 2 and 3, the handle assembly 12 includes right and left hemi-portions 15a, 15b, respectively. The right and left hemi-portions 15a and 15b may be mounted to one another through any known method of affixation including, for example, a plurality of pins mounted in a plurality of corresponding apertures or by other methods such as sonic welding or gluing. Each of the hemi-portions 15a, 15b are formed with a cavity 24 for accommodating various components of the instrument, all of which will be described in greater detail hereinbelow.

The right and left hemi-portions 15a, 15b of the handle assembly 12 are also formed with a bore 36 for receiving an elongated tube 38. As shown in FIG. 3, the proximal end of the elongated tube 38 extends from the proximal end of handle assembly 12, while the distal end of elongated tube 38 extends from the distal end of the handle assembly 12. As shown in FIG. 2, the distal end of elongated tube 38 is provided with a reduced outer diameter 47 and recessed portions 48 and 50. A tubular adapter 51 is mounted to the reduced diameter portion 47. This connection is accomplished by extending the reduced outer diameter 47 into the proximal end 52 of the tubular adapter 51.

With continuing reference to FIG. 2, upper cooperating jaw member 28 includes a plurality of connecting members 54 which enables a pivotal connection between the upper jaw member 28 and the tubular adapter 51. This connection is accomplished by extending connecting members 54 into corresponding slots 58 provided in the distal end of tubular adapter 51. Thereafter, the upper cooperating jaw member 28 is pivotably secured to the tubular adapter 51 by a pivot pin which is slidably received through apertures which are provided in the open slots 58 and in the plurality of connecting members 54. Additionally, the upper cooperating jaw member 28 defines an inner cavity portion 64 preferably having teeth 66 formed along the outer periphery thereof configured and dimensioned to secure and engage with tissue, which will be discussed in greater detail hereinbelow.

The lower cooperating jaw member 30 is formed with a hemi-cylindrical portion 68 at its proximal end 70. The hemi-cylindrical portion 68 is configured and dimensioned to extend within the distal end of tubular adapter 51. Additionally, the lower cooperating jaw member 30 defines an inner cavity 72. A cutting blade track 74 in the lower jaw 30 guides the blade cutting member 34 which reciprocally translates in the cutting blade track 74. Blade cutting member 34 is preferably flexible and capable of conforming to an arcuate configuration as shown in FIG. 2, but may be made of any suitable material which can be configured to cut tissue and to fit into cutting blade track 74.

The blade cutting member 34 extends into the recessed portions 48, 50 of elongated tube 38, and is received through an inner race 82 defined by the tubular adapter 51. The cutting member 34 has opposed ends 78, 80, wherein each end is disposed at a spaced relationship from the outer surface 76 of the proximal end of elongated tube 38. The cutting blade track 74 is conformed to receive the blade cutting member 34 at a distal end 84 of the lower cooperating jaw member 30. In particular, reciprocating movement of the cutting member 34 is restrained to follow cutting blade track 74. The movement of blade cutting member 34 with respect to distal end 84 is preferably arcuate. Elongated slots 90 and 92 are provided in the blade member 34 and are in communication with apertures 94, 96 provided in the lower jaw 30 such that restraining pins 98 and 100 pass through slots 90 and 92, respectively, and are fixed in apertures 94 and 96. Restraining pins 98, 100 restrain the translational movement of the blade member 34 within the cutting blade track 74 of the lower cooperating jaw member 30. Additionally, the portion of the elongated blade member 34 disposed in the inner cavity 72 of the lower jaw member 30 is provided with a plurality of teeth 5 configured to engage and cut tissue in response to translational movement of the cutting blade 34.

The second actuation mechanism 19 includes fight and left actuation arms 102, 104 and handle member 32. The second actuation mechanism 19 allows for remote actuation of the blade cutting member 34. As illustrated in FIG. 2, a top end 110 of handle member 32 is formed with a cutout 112 which defines upstanding sidewalls 113, 114. An elongated portion 116 of trigger 26 travels between the sidewalls 113, 114, and is retained by a pivot pin 118 which is mounted in apertures provided in the left hemiportion 15b and fight hemi-portion 15a of the handle assembly 12. Pivot pin 118 extends through elongated slot 124 provided on the elongated portion 116 of the trigger 26, and is secured in a corresponding mounting aperture 126 provided in the left hemi-portion 15b and a corresponding mounting aperture in the right hemi-portion 15a of the handle assembly 12. Thus, the handle member 32 pivots about the pivot pin 118 while the trigger 26 translates longitudinally intermediate the sidewalls 113, 114 of the top end 110 of handle member 32. In the embodiment of FIG. 2, the means for effectuating movement of the blade cutting member 34 is the right and left actuation arms 102, 104 and handle member 32.

Handle member 32 further includes yoke member 138, extending therefrom. A roller 139 is held in yoke member 138 by a pin 141 which passes through the center of roller 139 and is secured in mounting apertures 151, 153 of yoke member 138. Right and left actuation arms 102, 104 are pivotally mounted within the cavity portion 24 of the handle assembly 12 by a pivot pin 127 extending through apertures 128, 130. Pivot pin 127 is secured in apertures 132, 135 provided in the bottom ends of the fight and left hemi-portions 15a, 15b, respectively. Retraction of handle member 32 causes roller 139 to engage left actuation ann 104 thereby pivoting left actuation arm 104 about pivot pin 127 in the proximal direction.

To enable spring biased actuation of the handle member 32, proximal ends of cooperating springs 106, 108 are mounted within cut-outs 148, 150 provided in the left actuation arm 104 by fasteners 147, 149, while distal ends of the cooperating springs 106, 108 are mounted within a cavity 160 provided in the left hemi-portion 15b of the handle assembly 12 by a fastener 161 secured in a corresponding aperture provided in the cavity portion 160.

A rocker assembly 88 includes a rocker mount block 164 and a rocker member 174 which functions to move cutting blade member 34 under tension. The rocker mount block 164 is secured in a corresponding cut-out portion 166 provided in the left hemi-portion 15b of the handle assembly 12 by a fastener 168. The rocker member 174 is pivotably connected within sidewalls 176, 177 which project from the distal end of the rocker mount block 164. Pivot pin 180 extends through apertures provided on the distal end of the mount block 164 and through an aperture 184 provided on rocker member 174. As best illustrated in FIG. 3, the rocker mount block 164 is mounted intermediate the right and left actuation arms 102, 104 in the cavity portion 24 of the handle assembly 12. Referring again to FIG. 2, contact surfaces 170, 172 of rocker member 174 sit in cutouts 186, 188 of the actuation arms 102, 104. Cutouts 186 and 188 each have ball bearing pressed into their centers (not shown), which ride on contact surfaces of rocker member 174.

With continuing reference to FIG. 2, blade mounting blocks 187, 189 are fastened to top ends 190, 192 of the fight and left actuation arms 102, 104 by threaded mounting screws 191,193 in order to facilitate interconnection of the elongated cutting blade 34 to the right and left actuation arms 102, 104. To further secure this connection, threaded nuts may also be used in conjunction with the proximal ends of threaded mounting screws 191,193. The opposed ends 78, 80 of the blade cutting member 34 are fixed within blade slots 200, 201 which are provided in the blade mounting blocks 187, 189. This fixed connection enables the blade cutting member 34 to reciprocally translate relative to the longitudinal axis of the elongated tube 38 in response to movement of the actuation arms 102, 104 being effected by pivotal movement of the handle member 32, which is discussed in greater detail hereinbelow.

Figure 3A:
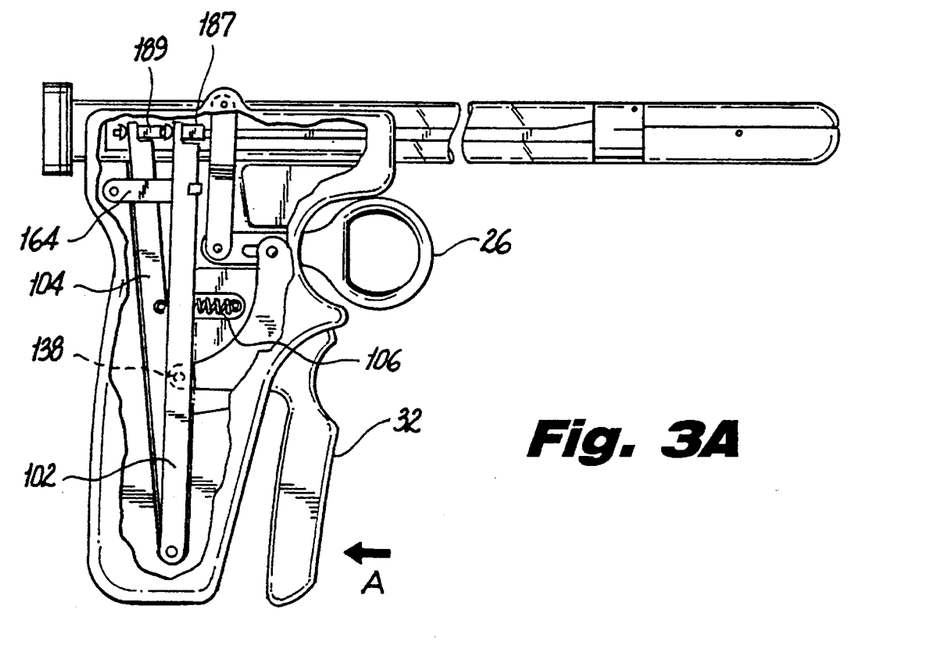
FIG. 3A is a side elevational view in partial cross-section of the surgical morcellator apparatus of FIG. 1 with the handle member in a first position.
Figure 3B:
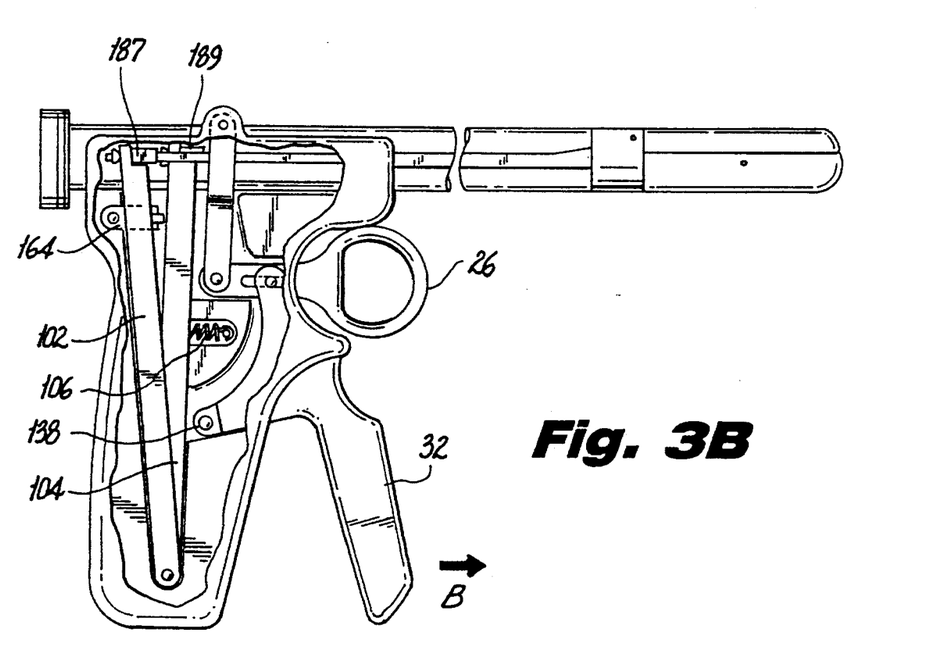
FIG. 3B is a side elevational view in partial cross-section of the surgical morcellator apparatus of FIG. 1 with the handle member in a second position.

Referring now to FIG. 3A in conjunction with FIG. 2, as handle member 32 is urged in the direction of arrow "A" by the user, roller 139 which is held in yoke member 138 of handle member 32, engages and drives left actuation arm 104 proximally. The end 80 of blade cutting member 34 is fastened to left actuation arm 104 via blade mounting block 189, therefore, as the left actuation arm is moved proximally, the end 80 of the blade cutting member 34 is also moved proximally. The movement of end 80 proximally causes blade cutting member 34 to travel in the direction of end 80 in cutting blade track 74 thereby pulling blade end 78 distally. The end 78 of blade cutting member 34 is fastened to fight actuation arm 102 via blade mounting block 187, therefore as the end 78 of blade cutting member 34 is moved distally, right actuation arm 102 is also moved distally. As fight actuation arm 102 is moved distally, the ball beating in cutout 186 of fight actuation arm 102 fides on contact surface 170 of rocker member 174, rotating the rocker member 174 to the left. Referring now to FIGS. 3B and 2, when handle member 32 is released in the direction of arrow "B", springs 106 and 108 which are mounted within cut-outs 148, 150 of the left actuation arm 104 pull left actuation arm 104 distally. The ball beating in cutout 188 of left actuation arm 104 fides on contact surface 172 in rocker member 174, thereby rotating the rocker member 174 to the right. The rotation of rocker member 174 to the fight forces contact surface 170 to drive fight actuation arm 102 proximally via cutout 186. Proximal motion of fight actuation arm 102 pulls blade end 78 proximally under tension.

Referring to FIGS. 2 and 3, the first actuation mechanism 17 includes the trigger 26, a Y-shaped pivot shank 250 and a pair of cooperating control rods 252, 254. The first actuation mechanism 17 allows for remote actuation of one or both of the cooperating jaw members 28, 30. The pivot shank 250 and pair of cooperating control rods 252, 254 operate to link at least one of the cooperating jaw members 28, 30 to the trigger 26. The control rods 252, 254 are recessed in tracks formed on elongated tube 38. Bottom portion 256 of the pivot shank 250 pivotably mounts to the proximal portion of the trigger 26, whereupon the proximal portion of the trigger 26 extends within slot 262 provided at the bottom portion 256 of the Y-shaped pivot shank 250. Facilitating this pivotable connection, pivot pin 264 extends through apertures located on the bottom portion of the pivot shank 250 and through a corresponding aperture 270 located on the proximal portion of trigger 26. In the embodiment of FIGS. 2 and 3, the actuation means for providing remote actuation of one or both of the cooperating jaw members 28, 30 between an open position and a closed position is the trigger 26, the Y-shaped pivot shank 250 and the cooperating control rods 252, 254.

The Y-shaped pivot shank 250 effectively straddles the outer surface 76 of the elongated tube 38 such that the elongated blade member 34 is disposed intermediate the pivot shank 250 and the elongated tube 38. The substantially parallel top ends 272, 274 of the Y-shaped pivot shank 250 are pivotably fastened within raised portions 276, 278 which are integral with the fight and left hemi-portions 15a, 15b, respectively, of the handle assembly 12. The proximal ends of the cooperating control rods 252, 254 fasten in corresponding apertures 284, 286 provided at a spaced distance from the top ends 272, 274 of the pivot shank 250. To accomplish such fastening, threaded screws 288, 290 extend proximally through the apertures 284, 286 of the Y-shaped shank 250 and threadingly engage the proximal ends of the control rods 252, 254. To further secure this connection, threaded nuts may be used in conjunction with the proximal ends of threaded screws 288, 290.

The cooperating control rods 252, 254 extend along the outer surface 76 of the elongated tube 38 from the tube's proximal end to the recessed portions 48, 50 at the distal end of the elongated tube 38. At the distal end of the elongated tube 38, the cooperating control rods 252, 254 extend into the recessed portions 48, 50 and through the inner race 82 of tubular adapter 51. The distal ends of the cooperating control rods 252, 254 project from the distal end of tubular adapter 51 and operatively associate with the proximal end of the upper cooperating jaw member 28. In particular, through manipulation of the trigger 26, corresponding pivotable movement of the Y-shaped pivot shank 250 is effected which, in turn, projects and retracts the control rods 252, 254 relative to the longitudinal axis defined by elongated tube 38. This movement actuates the upper jaw member 28. Thus, when the distal ends of the cooperating control rods 252, 254 project from the distal end of the tubular adapter 51, the upper jaw member 28 is actuated towards an open position, as shown in FIG. 3. When the distal ends of the cooperating control rods 252, 254 are caused to retract towards the proximal end of the connecting member 54, the upper jaw member 28 is actuated towards a closed position substantially parallel to the longitudinal axis of the elongated tube 38, as substantially shown in FIG. 7.

A sealing valve assembly 296 suitable for use in endoscopic procedures is provided at the proximal end of the elongated tube 38 to provide access to bore 133 of the elongated tube 38.

Right and left blade covers 300, 302 are preferably provided along the outer surface 76 of the elongated tube 38 such that the elongated cutting blade 34 is disposed intermediate a blade cover 300, 302 and the outer surface 76 of the elongated tube 38. The distal ends of the right and left blade covers 300, 302 are provided with an enlarged configuration being dimensioned to effectively cover the recessed portions 48, 50 at the distal end of the elongated tube 38. Right and left blade covers 300, 302 are affixed to the outer surface 76 of the elongated tube 38 through any known method of affixation including, for example sonic welding or gluing.

Figures 4, 5:
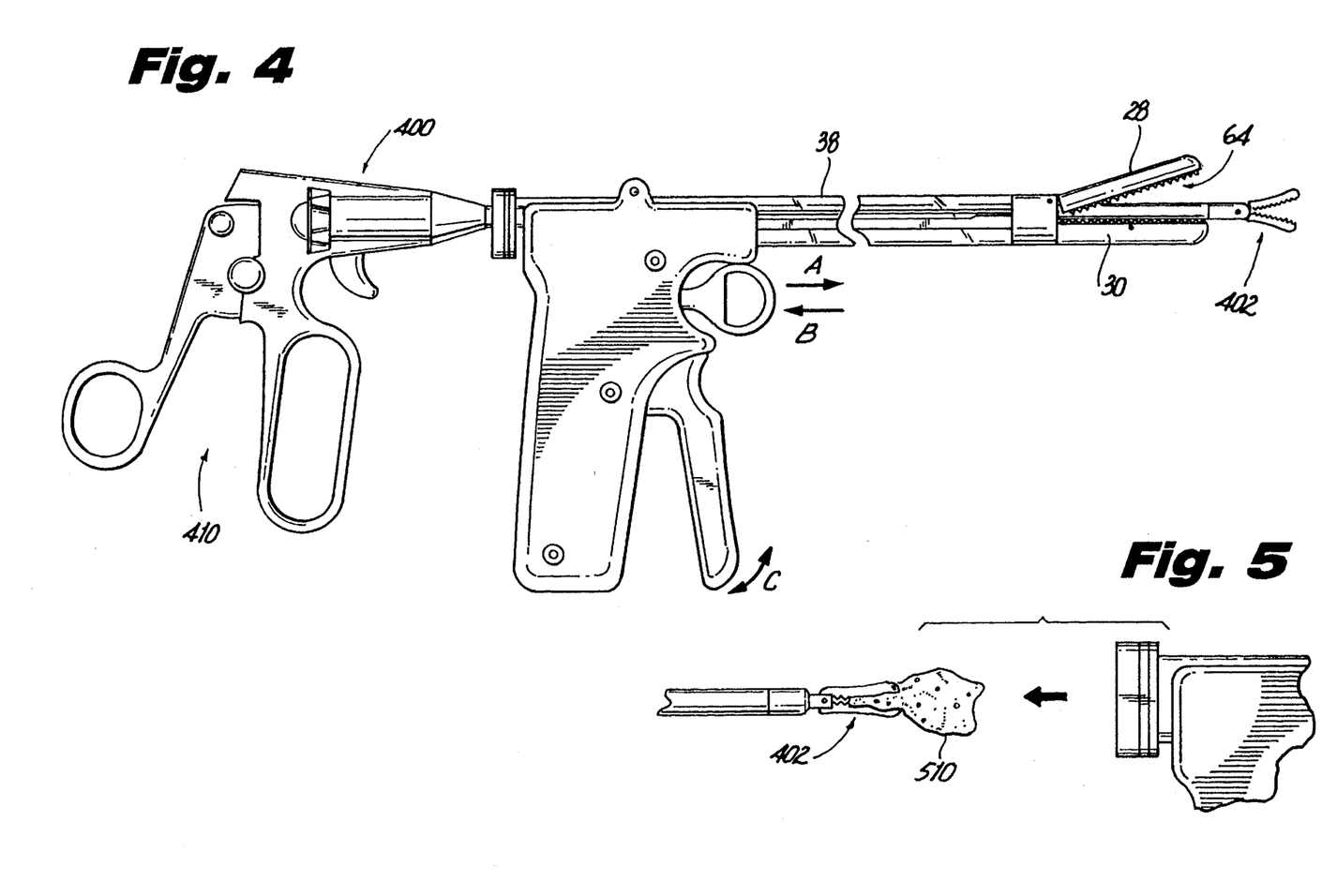
FIG. 4 is a side elevational view of the surgical morcellator apparatus in conjunction with an endoscopic surgical grasping instrument.
FIG. 5 is an illustration of a fragmented tissue part being removed from the proximal end of the surgical morcellator apparatus by the endoscopic gripping instrument of FIG. 4.

Turning to FIG. 4, the elongated tube 38 of the morcellator apparatus 10 is dimensioned and configured to receive a surgical instrument 400, such as an endoscopic grasper, one such device being disclosed in U.S. patent application Ser. No. 08/068,296 filed May 27, 1993 which is hereby incorporated by reference, and which is a continuation of U.S. patent application Ser. No. 07/593,670 filed Oct. 5, 1990. The surgical instrument 400 can be slidably received within bore 133 (FIGS. 8–9) of the elongated tube 38, via a valve assembly 296, such that a tool member 402 which is located at a distal end of the surgical instrument 400, is extendible from the distal end of cooperating jaw members 28, 30 when said jaw members are in the open position. Bore 133 is configured to allow both the passage of surgical instrument 400 and a sample of target tissue 500 therethrough. Handle mechanism 410, located at a proximal end of the surgical grasping instrument 400, remotely actuates the tool member 402 between an open position and a closed position. It is within the scope of the present application to substitute the surgical grasping instrument 400 with other surgical instruments dimensioned and configured to be slidably received within the elongated tube 38 and having a tool member 402 which projects from the distal end of the cooperating jaw members 28, 30.

Figure 6:
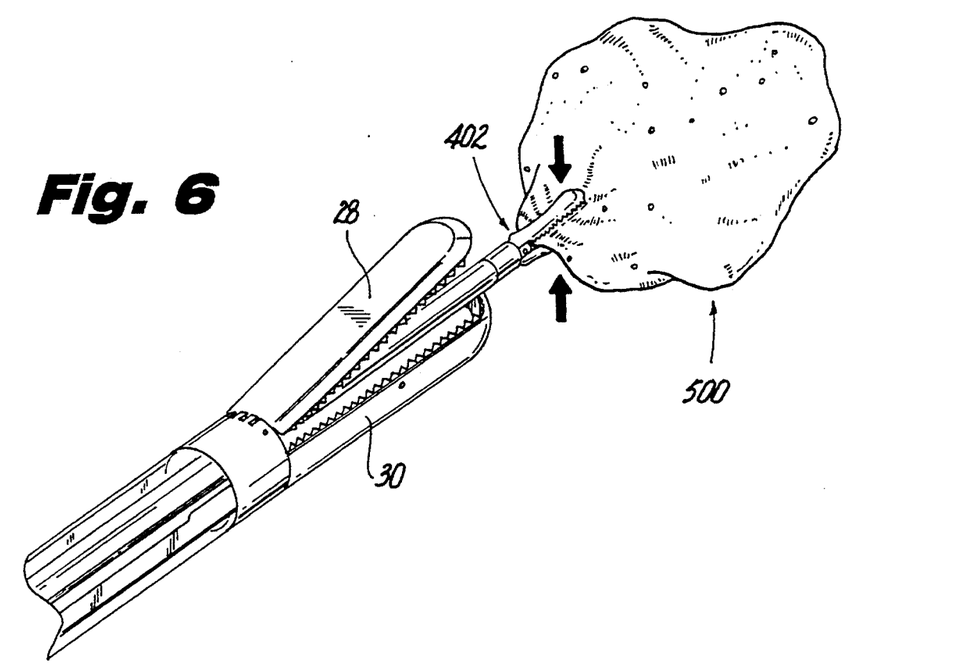
FIGS. 6 and 7 illustrate the capture of tissue during a morcellation procedure employing the surgical morcellator in cooperation with the endoscopic surgical gripping instrument.
Figure 7:
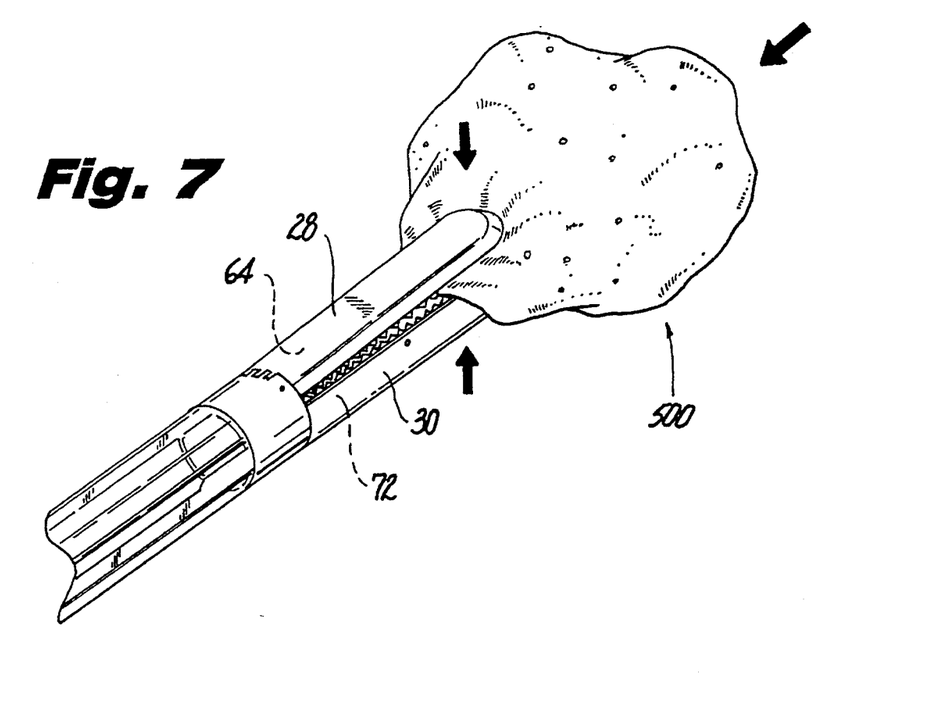

Referring to FIGS. 5–7, the surgical grasping instrument 400 accesses and secures target tissue within the rigid inner cavities 64 and 72 defined by the cooperating jaw members 28, 30, respectively, in preparation for the morcellation of the target tissue 500. Preferably, after completion of the morcellation procedure, the fragmented tissue part 510 may be retracted from the body cavity and the morcellator apparatus 10, by proximally retracting the surgical grasping instrument 400 having the fragmented tissue 510 secured within the tool member 402, from the proximal end of the morcellator apparatus 10.

In operation, to introduce the morcellator apparatus 10 into the abdominal cavity of a patient during an endoscopic morcellation procedure, the upper and lower cooperating jaw members 28, 30 should be in the closed position, such that the upper cooperating jaw member 28 is aligned with the longitudinal axis defined by the elongated body portion 14 of the instrument 10 to facilitate its insertion through an opening or a trocar or cannula device. Once the instrument has been extended into the patient's abdominal cavity, the distal end of the cooperating jaw members 28, 30 should be positioned in close proximity to the target tissue 500.

Referring to FIGS. 4 and 6, with the upper and lower cooperating jaw members 28, 30 advanced to the target tissue 500, the user actuates the upper jaw member 28 to its open position by moving the trigger portion 26 in the direction indicated by arrow "A" in FIG. 4. The user then inserts the surgical grasping instrument 400 through the valve assembly 296 at the proximal end of and through the elongated tube 38, until the tool member 402 of the instrument 400 projects from the distal end of the cooperating jaw members 28, 30. The tool member 402 then engages the target tissue 500 through manipulation of the handle mechanism 410 of the surgical grasping instrument 400.

Figure 8:
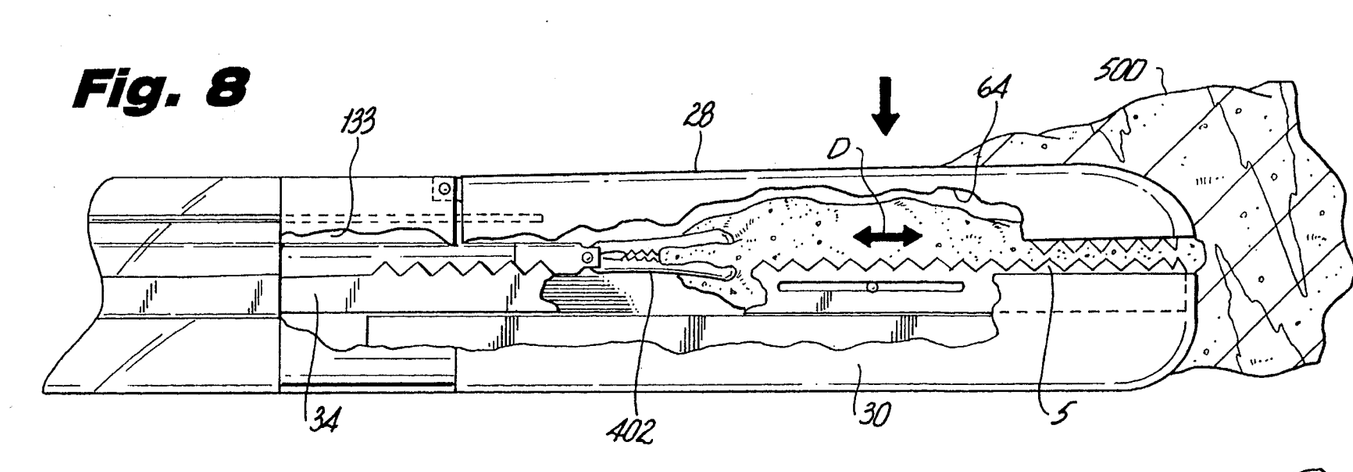
FIG. 8 is a side elevational view in partial cross-section of the jaw assembly of the morcellator device illustrated in FIG. 4 during the fragmenting of the tissue part.

Referring to FIGS. 7 and 8, the target tissue 500, or a portion thereof, is retracted into the rigid inner cavities 64, 72 by retracting the surgical grasping instrument 400 in a proximal direction relative to the morcellator apparatus 10, until the tool member 402 of the surgical grasping instrument 400 is disposed within the rigid inner cavities 64, 72 of the cooperating jaw members 28, 30. At such a time, the upper jaw member 28 is actuated to its closed position, therein securing the target tissue within inner cavities 64, 72. Actuation of the upper jaw member 28 to its closed position is achieved by moving the trigger portion in the direction indicated by arrow "B", as shown in FIG. 4.

Figure 9:
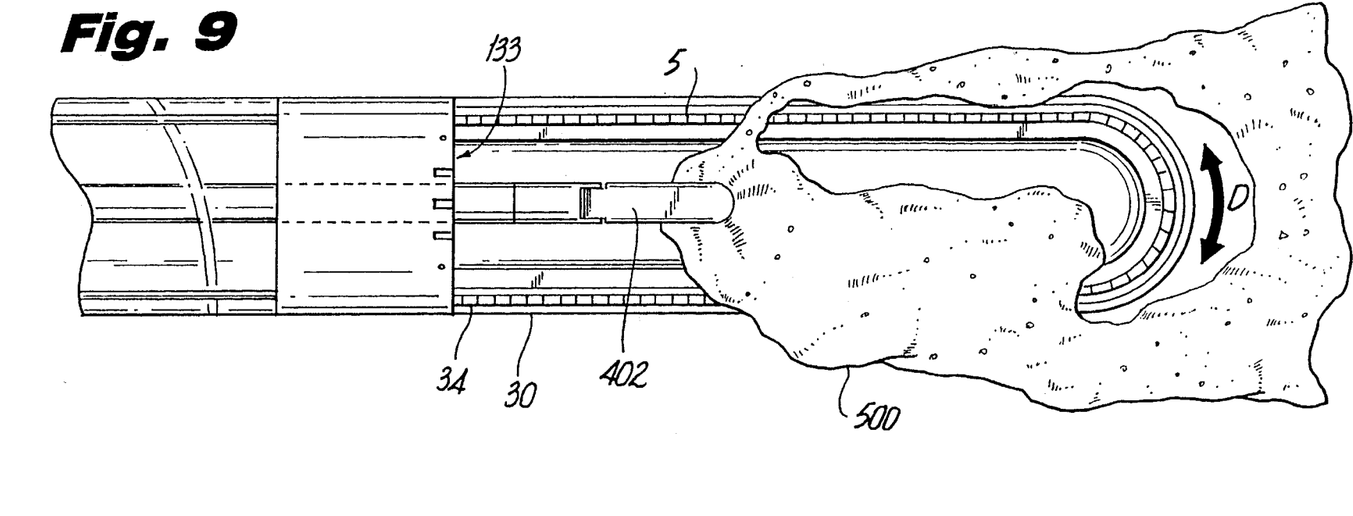
FIG. 9 is a top planar view with the top jaw member removed of the surgical morcellator apparatus of FIG. 8.

Referring to FIGS. 8 and 9, morcellation of the target tissue 500 is achieved by actuating the handle member 32 in the direction indicated by arrow "C" (see FIG. 4) which effectuates the arcuately configured cutting blade 34 to translate in the direction indicted by arrow "D", whereupon the cutting blade 34 cuts and separates the target tissue 500 within the rigid inner cavities 64, 72 of the cooperating jaw members 28, 30 from a tissue body. Afterwards, the fragmented tissue part 510 may be removed from the patient's abdominal cavity by proximally retracting the surgical grasping instrument 400, having the fragmented tissue 510 secured thereto, from the morcellator apparatus 10, as illustrated in FIG. 5. Alternatively, the user may remove the morcellator apparatus 10 from the abdominal cavity of the patient, via the trocar or cannula device, whereupon the fragmented tissue part 510 can be removed from within the inner cavity of the cooperating jaw members 28, 30.

The morcellator instrument described herein is compact, lightweight and easy to use. It is intended to enable the surgeon to use the instrument with one hand, thus freeing the other hand for performance of surgical tasks.

It will be understood that various modifications may be made to the embodiments described herein. For example, although described in conjunction with a surgical grasping instrument (400), such a surgical grasping instrument need not always be utilized with the morcellator. In addition, although the blade cutting member has been shown in an arcuate configuration, other configurations would also be suitable. Therefore, the above description should not be construed as limiting, but merely as exemplifications of preferred embodiments. Those skilled in the art will envision other modifications within the scope and spirit of the claims appended hereto.

What is claimed is:

1. A surgical apparatus for fragmenting tissue comprising:
    a tissue grasping mechanism positioned adjacent a distal end of the surgical apparatus and movable between an open and closed position and defining a tissue receiving cavity therein;
    a cutting member disposed in and around a periphery of the tissue receiving cavity in a position to morcellate tissue therein; and
    a first actuation mechanism operably connected to the tissue grasping mechanism for remotely opening and closing the tissue grasping mechanism;
        wherein the tissue grasping mechanism holds the tissue preparatory to the morcellating of the tissue by the cutting member.

2. A surgical apparatus as recited in claim 1, wherein the tissue grasping mechanism includes a pair of cooperating jaw members configured for securing the tissue.

3. A surgical apparatus as recited in claim 1, wherein the tissue receiving cavity is substantially semi-cylindrical.

4. A surgical apparatus as recited in claim 1, wherein the cutting member includes a flexible cutting blade.

5. A surgical apparatus as recited in claim 4, further comprising a second actuation mechanism operatively connected to the cutting blade for effecting movement of the cutting blade.

6. A surgical apparatus as recited in claim 5, wherein the movement of the cutting blade is reciprocal with respect to the tissue receiving cavity.

7. A surgical apparatus comprising:
    a handle assembly;
    a body portion extending from the handle assembly and defining a longitudinal axis;

first and second jaw members mounted to the body portion for movement between an open position and a closed position, at least one of the first and second jaw members defining a tissue receiving cavity therein, such that when the first and second jaw members are in the closed position and prior to morcellating, said tissue receiving cavity being substantially closed by jaws such that tissue disposed in the tissue receiving cavity is substantially encapsulated by the first and second jaw members;

a cutting member internal of at least one of the jaw members; and extending into and around a periphery of said tissue receiving cavity; and a jaw actuation mechanism connected to the first jaw member;

wherein the first jaw member is actuated between the open and the closed position by the jaw actuation mechanism.

8. A surgical apparatus as recited in claim 7, wherein the tissue receiving cavity is substantially semi-cylindrical.

9. A surgical apparatus as recited in claim 7, wherein at least one of the first and second jaw members is provided with teeth.

10. A surgical apparatus as recited in claim 7, wherein the cutting member includes a flexible cutting blade.

11. A surgical apparatus as recited in claim 7, further comprising a blade actuation mechanism connected to the cutting member for effectuating reciprocating movement of the cutting member within the tissue receiving cavity.

12. A surgical apparatus as recited in claim 11, wherein the blade actuation mechanism includes a handle member pivotally connected to the handle assembly and at least one actuation arm, the actuation arm interconnecting the handle member to the cutting member.

13. A surgical apparatus as recited in claim 7, wherein the jaw actuation mechanism includes a trigger member connected to the handle assembly and at least one linkage member, the at least one linkage member operatively connecting the trigger member to the first jaw member.

14. A surgical apparatus as recited in claim 7, wherein the body portion includes a bore portion having a longitudinal axis defined by the longitudinal axis of the body portion for accessing the cutting member.

15. A surgical apparatus as recited in claim 14, wherein the bore portion is dimensioned so as to be capable of pulling fragmented tissue therethrough.

16. A surgical apparatus as recited in claim 15, wherein the bore portion is dimensioned for reception of a grasping member therethrough.

17. A surgical apparatus as recited in claim 7, wherein the body portion is dimensioned and configured for insertion through a trocar cannula.

18. A surgical apparatus comprising:

a first handle assembly;

a first elongated tubular body portion extending from the handle assembly and defining a longitudinal axis, the first body portion further including a longitudinal bore portion for receiving a grasping instrument therethrough;

a first tool assembly connected to a distal end portion of the first body portion, the first tool assembly including first and second jaw members, the first jaw member being pivotally connected to the distal end of the first body portion, the second jaw member defining a tissue receiving cavity and having a cutting member disposed in and around a periphery of the tissue receiving cavity in a position to morcellate tissue therein;

jaw actuation means for actuating the first jaw member between an open and a closed position; and means for effectuating movement of the cutting member with respect to the longitudinal axis of the first body portion.

19. A surgical apparatus comprising:

a first handle assembly;

an elongated tubular body portion extending from the handle assembly and defining a longitudinal axis, the tubular body portion further including a longitudinal bore portion;

a tool assembly connected to a distal end portion of the tubular body portion, the tool assembly including a pair of cooperating jaw members and extending into and around a periphery of said tissue receiving cavity having an internal cutting member;

a cutting member actuator mounted within the tubular body portion wherein movement of the actuator moves the cutting member relative to the jaw members;

a grasping instrument inserted into the longitudinal bore portion, the grasping instrument having an elongated body portion including a tool assembly connected to a distal end of the elongated body portion of the grasping instrument, and a handle assembly connected to a proximal end of the elongated body portion of the grasping instrument to effectuate remote actuation of the grasping instrument tool assembly between an open position and a closed position.

20. A surgical apparatus as recited in claim 18, further comprising a value assembly connected to the longitudinal bore portion and adjacent a proximal end of the first body portion.

21. A surgical apparatus as recited in claim 18, wherein the cutting member includes a flexible cutting blade.

22. A surgical apparatus as recited in claim 21, wherein the cutting blade is provided with a plurality of serrated cutting members.

23. A surgical apparatus as recited in claim 18, wherein the first body portion is dimensioned and configured for endoscopic utilization.

* * * * *